United States Patent [19]

Bajada

[11] Patent Number: 4,823,806
[45] Date of Patent: Apr. 25, 1989

[54] APPARATUS FOR TESTING THE SENSORY SYSTEM ON HUMANS OR ANIMALS

[76] Inventor: Serge Bajada, 30 Holdsworth Street, Fremantle, Western Australia, Australia, 6160

[21] Appl. No.: 86,096
[22] PCT Filed: Nov. 18, 1986
[86] PCT No.: PCT/AU86/00348
§ 371 Date: Apr. 28, 1987
§ 102(e) Date: Apr. 28, 1987
[87] PCT Pub. No.: WO87/02888
PCT Pub. Date: May 21, 1987

[30] Foreign Application Priority Data
Nov. 18, 1985 [AU] Australia .............................. PH3457

[51] Int. Cl.$^4$ .............................................. A61B 17/34
[52] U.S. Cl. .................................... 128/744; 604/110; 128/743; 128/329 R
[58] Field of Search ................................. 128/743–744, 128/329 R, 333; 604/110–111, 289–290

[56] References Cited

U.S. PATENT DOCUMENTS

| | | | |
|---|---|---|---|
| 2,704,539 | 3/1955 | Fisher | 128/744 |
| 3,074,395 | 1/1963 | Kevorkian | 128/744 |
| 3,343,541 | 9/1967 | Bellamy | 604/111 |
| 3,902,475 | 9/1975 | Begg et al. | 128/637 |
| 4,438,770 | 3/1984 | Unger et al. | 128/637 |
| 4,483,348 | 11/1984 | Sher | 128/743 |

OTHER PUBLICATIONS

NASA Tech. Brief; Modified Algesimeter Provides Accurate Depth Measurements; 12–1966.

Primary Examiner—Kyle L. Howell
Assistant Examiner—Angela D. Sykes
Attorney, Agent, or Firm—Kerkam, Stowell, Kondracki & Clarke

[57] ABSTRACT

An apparatus (10) for testing the sensory system in humans or animals comprising housing parts (12, 14) which are jointed together in volume defining manner to form a housing. The housing has a gap formed by recesses (64, 66) in the housing parts, and encloses a disc (26) having mounted thereon a plurality of pins (40) with tips extending beyond the periphery of the disc (26). The pins (40) are held captive in the housing and cannot be removed therefrom. The disc (26) is arranged to be rotated incrementally by a manually operable knob (30) so as to present the pins (26) in sequence to the gap.

12 Claims, 6 Drawing Sheets

APPARATUS FOR TESTING THE SENSORY SYSTEM ON HUMANS OR ANIMALS

DESCRIPTION

The present invention relates to an apparatus for testing the sensory system in humans or animals.

FIELD OF THE INVENTION

It is known to use pins to test the sensory system in humans or animals. However, there is a risk of a pin being used on more than one subject unless suitable precautions are taken. If a pin is used on more than one subject there may be a risk of cross-infection. Thus, there is a need for a means for providing pins for use in testing the sensory system in humans or animals by which the risk of one pin being used on more than one subject is reduced.

SUMMARY OF THE INVENTION

In accordance with one aspect of the present invention there is provided an apparatus for testing the sensory system in humans or animals, which comprises an apparatus for testing the sensory system in humans or animals characterized in that it comprises a volume enclosing housing containing a plurality of pins, said pins being held captive in the housing and being so mounted as to have tips sequentially available at a point of use for testing the sensory system in humans or animals, and wherein once a pin has been used on a subject the used pin is movable to a location in the housing at which the tip of the used pin is inaccessible.

BRIEF DESCRIPTION OF THE DRAWINGS

The present invention will now be described, by way of example, with reference to the accompanying drawings, in which.

DESCRIPTION OF THE INVENTION

Figure 1:
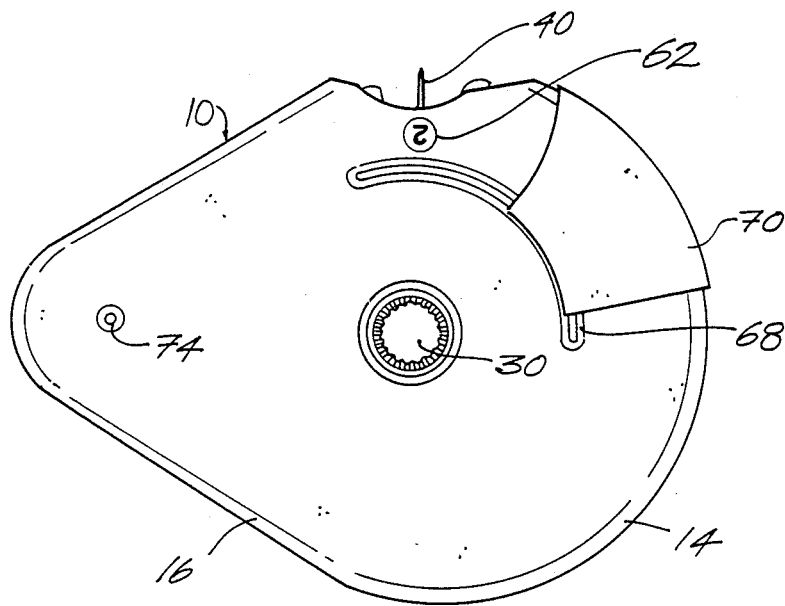
FIG. 1 is a plan view of an apparatus in accordance with the present invention.

In the drawings there is shown an apparatus 10 for testing the sensory system in humans or animals. The apparatus 10 comprises an outer volume enclosing housing having a first lower housing part 12 and a second upper housing part 14. The housing parts 12 and 14 each have a peripheral rib 16 and are of complementary shape. Each part 12 and 14 has a relatively wide portion with a large arcuately shaped end and a relatively narrow portion with tapering sides which converge towards a small arcuately shaped end. The housing parts 12 and 14 are arranged to be engaged together with their peripheral ribs 16 in abutting relation so that the parts 12 and 14 define an enclosed volume. In this connection, the housing part 12 is provided adjacent its large arcuately shaped end with three spaced upstanding socket members 18 and adjacent its small arcuately shaped end with a pair of upstanding socket members 18. All of the socket members 18 are adjacent the rib 16 of the housing part 12.

Figure 6:
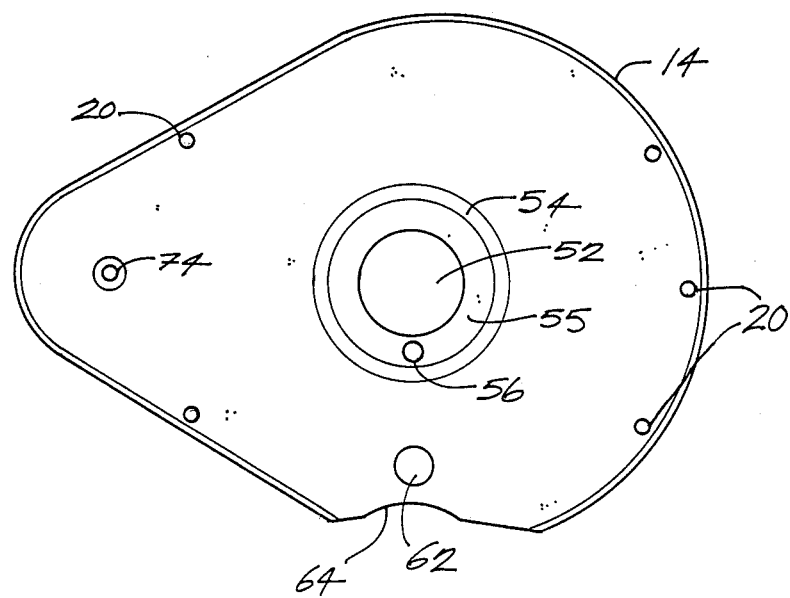
FIG. 6 is a view of the interior of an upper housing part of the apparatus of FIGS. 1 and 2.

Further, as can be seen in FIG. 6, the housing part 14 is provided adjacent its peripheral rib 16 with a plurality of posts 20. Each post 20 is located at a point corresponding with a respective socket 18 and is arranged to fit inside its respective socket 18. Further, the sockets 18 and the posts 20 are preferably arranged so that they firmly fit together. For example, the posts 20 could have enlarged ends whilst the sockets 18 could have constricted inlets so that when the housing parts 12 and 14 are presented to one another the sockets 18 and the posts 20 engage with a snap fit. Further, the housing part 12 contains on its interior face a first upstanding circular projection 22 which is surrounded by a second larger upstanding circular projection 24. The circular projection 22 is of greater height than the circular projection 24.

Figure 4:
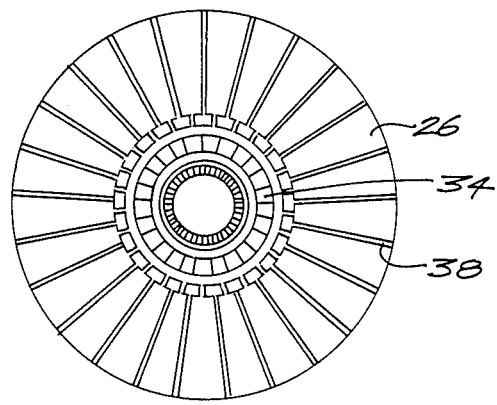
FIG. 4 is a plan view of a disc forming part of the apparatus of FIGS. 1 and 2, not containing any pins.
Figure 5:
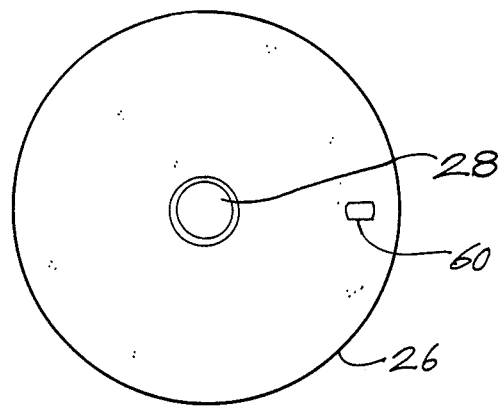
FIG. 5 is an underneath view of a disc forming part of the apparatus of FIGS. 1 and 2.

The apparatus 10 further comprises a circular disc 26 the underside of which can be seen in FIG. 4. The underside of the disc 26 contains a central recess 28 which is arranged to fit snugly over the circular projection 22 so as to positively locate and to support rotatably the disc 26 in the housing of the apparatus 10. The circular projection 24 forms a bearing surface for the disc 26 when it is engaged with the projection 22.

The upper face of the disc 26 is provided with a central knob 30. A circular ratchet 32 extends around the knob 30. The ratchet 32 comprises a plurality of teeth which have an asymmetrical profile whereby one side of a tooth is sloped relative to the upper surface of the disc 26 and the other side is substantially vertical thereto.

Figure 2:
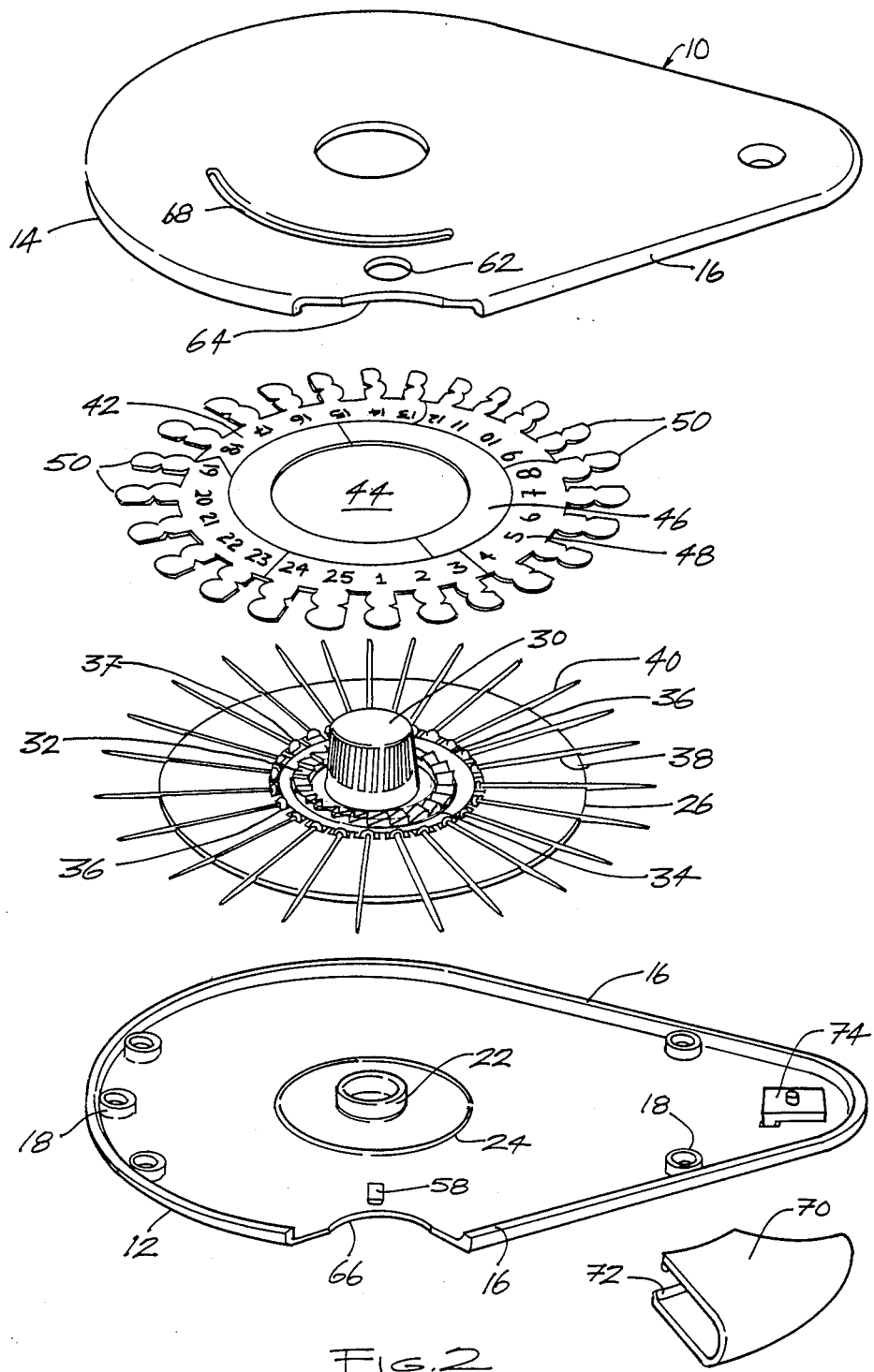
FIG. 2 is an exploded view of the apparatus of FIG. 1.

A circular groove 34 extends around the ratchet 32. The groove 34 is divided by dividers 36 into a plurality of discrete pockets 37 arranged to receive individual heads of pins as will be described. Further, a radial groove 38 extends outwardly from each pocket 37 to the periphery of the disc 26. As can be seen in FIG. 2 each pocket 37 and its corresponding radial groove 38 is arranged to receive a respective pin 40 with a head of the pin located in the pocket 37 and the tip of the pin 40 being located outwardly of the disc 26.

Figure 3:
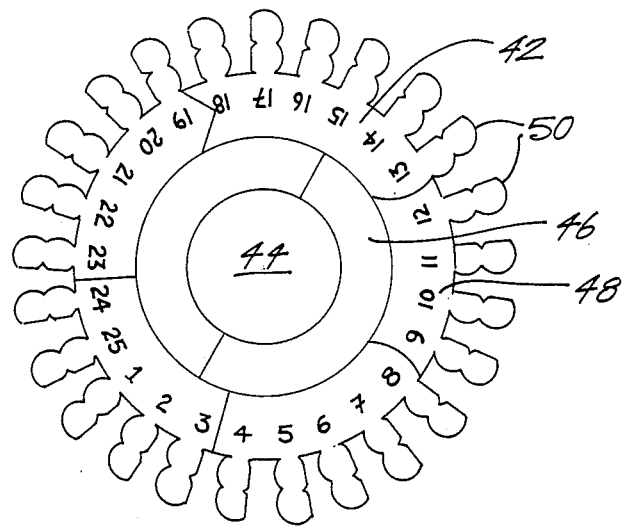
FIG. 3 is a plan view of an adhesive cover sheet forming part of the apparatus of FIGS. 1 and 2.

The apparatus 10 further comprises an adhesive cover sheet 42 which can best be seen in FIG. 3. The cover sheet 42 may be formed of paper which has a first coated side and a second adhesive side. The cover sheet 42 is scored so as to have a central circular portion 44. A first annular portion 46 surrounds the portion 44 and is divided into two parts, a second annular portion 48 surrounding the annular portion 46 and divided into five parts, and a plurality of radially extending tabs 50 extending outwardly from the annular portion 48.

The housing portion 14 includes a centrally located aperture 52 and, on its interior face, an annular groove 54 extending around but spaced from the aperture 52. In the land 55 between the aperture 52 and the groove 54 there is located a single tooth 56. The tooth 56 has a profile complementary to the teeth of the ratchet 32 wherein one side is sloped to the land 55 and the other side is substantially vertical thereto. Still further, the interior of the housing part 12 is provided with a stop 58 which is arranged to engage with a corresponding stop 60 on the underside of the disc 26.

The stops 58 and 60 provide, in use, a reference point for the location of the disc 26 in the apparatus. In this connection, the annular portion 48 is preferably provided with spaced sequences of numbers as shown in FIG. 3 corresponding with respective pins 40.

Further, the scoring of the annular portion 48 is preferably done in such a way that, as can best be seen in FIG. 3, the individual parts of the portion 48 can only be joined together in one way. This ensures that the sequence of numbers runs correctly in the assembled product. The stops 58 and 60 are so arranged that the pin numbered one is presented first for use providing the relevant part of the annular portion 48 is correctly located on the disc 26. The housing part 14 contains an aperture 62 and a recess 64. The housing part 12 also contains a recess 66 of corresponding shape and size to the recess 64.

The recesses 64 and 66 each contain lateral portions of a low degree of curvature and an inner portion of a greater degree of curvature with shoulders between the portions of different curvature as can best be seen in FIG. 1.

In the assembled product, as seen in FIG. 1, the recesses 64 and 66 mate together. Further, as can be seen in FIG. 2, the formation of the recesses 64 and 66 removes the peripheral rib 16 from the margin of the parts 12 and 14. Thus, in the assembled products a gap is formed in the housing by the recesses 64 and 66. Still further, each housing part 12 and 14 contains in its external face an arcuate slot 68. A slidable U-shaped cover 70 is provided with inward facing projections 72 at the outer ends of its limbs. The projections 72 engage with respective slots 68 so that the cover 70 can be slid over from the gap formed by the recesses 64 and 66 when the apparatus 10 is not required for use and away from the said gap when the apparatus 10 is required for use.

Figure 7:
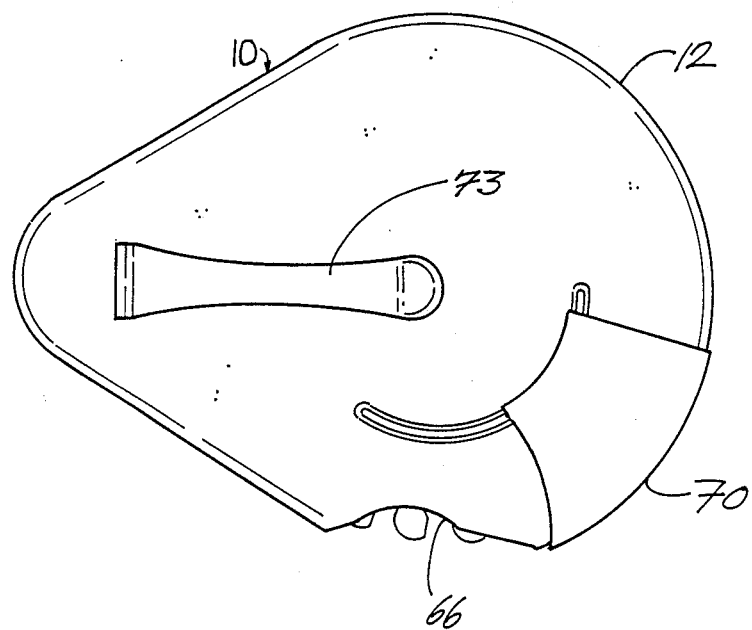
FIG. 7 is a view of the exterior of a lower housing part of the apparatus of FIGS. 1 and 2.
Figure 8:
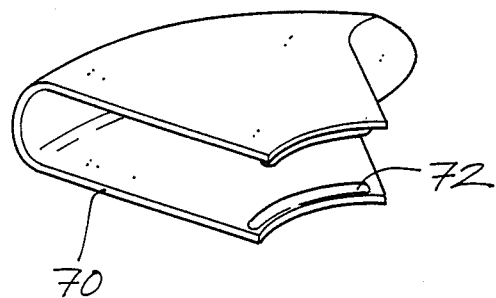
FIG. 8 is a perspective elevation of a slidable cover forming part of the apparatus of FIGS. 1 and 2.

Further, as can be seen in FIG. 7, the housing part 12 may be provided with a resilient clip 73 to enable the apparatus 10 to be clipped into a pocket or the like of a user.

The apparatus 10 is assembled by providing the housing parts 12 and 14 which are conveniently moulded from a plastics material.

Similarly, the disc 26 may be moulded from a plastics material.

A disc 26 is engaged with the housing part 12 by rotatable engagement of the aperture 28 with the circular rib 22. The disc 26 is so located that the stops 58 and 60 are in engagement. Previously or subsequently, a pin 40 is laid in each groove 38 with a head of each pin 40 resting in a respective pocket of the groove 34. As shown in FIG. 2 the tips of the pins 40 project outwardly of the periphery of the disc 26. Then the cover sheet 42 is pulled from a release sheet in parts. This is done so as to make the cover sheet 42 easy to handle. The central portion 44 may be removed first and discarded. Then the two parts of the first annular portion 46 may be removed from the release sheet and placed sequentially and not overlappingly over the disc 26 outwardly of the heads of the pins 40 in the groove 34. Then the five parts of the second annular portion 48 may be removed from the release sheet and placed sequentially and non-overlappingly over the disc 26 adjacent the periphery thereof. As can best be seen in FIG. 3 mating ends of the parts of the annular portion 48 are cut in a unique manner so that the annular portion can only be placed in one way on the disc 26 to achieve a complete annulus. This is important because, as described above, the annular portion 48 bears numbers each of which corresponds with respective pins 40 on the disc 26. The numbers on the annular portion 48 are arranged so as to be sequentially visible through the aperture 62 in use.

The annular portion 48 is so deposited on the disc 26 that with the stops 58 and 60 in engagement the number one is initially visible through the aperture 62.

Further, the teeth of the ratchet 32 and the tooth 56 form a ratchet which ensures that the disc 26 can only be rotated in one direction. Thus, the stops 58 and 60 are so arranged that the disc 26 can be rotated to separate the stops 58 and 60 and expose in sequential manner further numbered pins for use.

Further, the annular portion 48 has the radially extending tabs 50 projecting therefrom. The tabs 50 are each conveniently joined to the annular portion 48 by means of a perforated or otherwise weakened joint so that the tabs 50 can be readily removed when required as will be described. Each tab 50 is folded over the tip of a respective pin 40 so as to sheath the tip and protect it from dust.

Then the housing part 14 is placed over the assembly in such manner that the posts 20 engage firmly with respective sockets 18 so that the housing parts are firmly engaged together with their ribs 16 in abutting relation. Further, the tooth 56 is engaged with the rack 32 so that the disc 26 can only be rotated in one direction i.e. that in which the numbers visible in the aperture 62 increase.

The pins 40 are held captive in the apparatus 10 firstly by mating of the grooves 34 and 54. Further the pins 40 are held firmly in place by the cover sheet 42. Thus, once the housing parts 12 and 14 are engaged it is extremely difficult, if not impossible, to remove the pins 40 without dismantling the apparatus 10. In this connection, the apparatus 10 is preferably provided with a tamper indicator. This may take the form of a heat sensitive sealing means 74 which has two parts on respective housing parts 12 and 14.

When the apparatus 10 has been assembled heat can be applied to the exterior of the housing part 14 adjacent the sealing means 74 so as to fuse the two parts thereof. If the apparatus 10 is subsequently tampered with this will be evident from an inspection of the sealing means 74. In this way an operator can be confident, when the sealing means 74 is intact, that the pins in the apparatus 10 were placed therein at the time of manufacture and that the device has not been tampered with. The slidable cover is then engaged by means of the ribs 72 with the arcuate slots 68 so as to enable the gap formed by the recesses 64 and 66 to be covered when the apparatus is not in use. The assembled apparatus 10 is then subject to sterilisation procedures to make it ready for use.

At the outset when the device is fully assembled the pin 40 corresponding with the number one is in the gap formed by the recesses 64 and 66. The No. 1 pin 40 projects outwardly between the shoulders of the recesses 64 and 66. The tip of the No. 1 pin 40 is made accessible by moving the slidable cover 70 away from the gap. When it is desired to test the sensory system of a human or animal, the tab 50 of the No. 1 pin 40 is removed by an operator so as to expose the tip of the No. 1 pin 40.

The apparatus 10 can then be used by applying it to the skin of the subject so that the tip of the pin 40 contacts the nervous system and the response of the subject is noted by the operator.

Preferably, the apparatus 10 is used on areas of skin which are substantially flat so that the edges of the gap formed by the recesses 64 and 66 contact the skin and limit the degree of penetration of the pin 40. This is advantageous because for testing the sensory system only a small degree of penetration is required.

When an operator has finished testing a subject he can then rotate the disc 26 by means of the knob 30 through one increment as determined by engagement of the tooth 56 with the teeth of the ratchet 32. This moves the used No. 1 pin back into the interior of the housing so that it is inaccessible, the No. 2 pin becomes visible in the aperture 62 and the No. 2 pin becomes available for use at the gap formed by the recesses 64 and 66. If the operator should forget to do this immediately he can readily ascertain whether a pin 40 has been used by the presence or absence of a tab 50 on a pin 40. The process is repeated until the last pin 40 has been used at which point any further rotation of the disc 26 is prevented by re-engagement of the stop 58 and 60. In other words, once the disc 26 has completed a full circle the stops 58 and 60 re-engage with one another. The apparatus 10 is then discarded.

The slots 68 could have radial ridges extending from each end of each arcuate slot 68 to reduce the possibility of the slidable cover 70 being pulled off inadvertently. When the apparatus 10 is not in use the cover 70 is preferably slid over the slots 68 until the gap is closed.

From the above, it can be seen that the concept of the apparatus of the present invention involves delivering a pin, which is held stationary in one position on a rotating member, to a cut-out in a circular housing so that the pin can perform its function and then taking the pin back into the housing by virtue of the geometry of the apparatus.

Modifications and variations such as would be apparent to a skilled addressee are deemed within the scope of the present invention. For example, the pins 40 could be held captive by being moulded into the plastics material of the disc 26 or the pins 40 could be glued in place.

Also, the housing could have an externally mounted felt pad for testing different sensory perceptions to that of the pins.

Still further, the apparatus 10 could include a plurality of heat sealing means 74 to enhance the tamper-proof nature thereof. For example, one of the sockets 18 seen on the left in FIG. 2 and its corresponding pin 20 could be replaced by a heat sealing means 74. In this way, a heat seal would be provided at each end of the apparatus 10 which would make it ever more difficult to tamper with the apparatus 10 without leaving evidence thereof.

I claim:

1. An apparatus for testing the sensory system in humans or animals which comprises a volume enclosing housing having mounted therein a plurality of pins, means for holding said pins captive in the housing, said pins being arranged to have tips sequentially available at a point of use for testing the sensory system in humans or animals, and means for preventing tips of used pins being returned to the point of use wherein once a pin has been used on a subject, the used pin is movable away from the point of use such that the tip of a used pin is rendered inaccessible.

2. An apparatus according to claim 1, wherein the housing comprises a gap in its outer wall at which the tips of the pins are presented sequentially in such manner that they project outwardly of the housing for use.

3. An apparatus according to claim 1, wherein the pins are mounted on an assembly which is arranged to be moved incrementally in one direction only so at each incremental movement, a new pin is presented for use.

4. An apparatus according to claim 3, wherein the apparatus includes a ratchet engaged by a tooth to control the incremental movement.

5. An apparatus according to claim 3, wherein the pins are incrementally movable by means of an externally accessible manually operable control.

6. An apparatus according to claim 1, wherein the pins are mounted on a rotatably mounted disc with tips of the pins projecting radially outwardly of the disc.

7. An apparatus according to claim 6, wherein the pins have heads which are located in a pair of cooperating opposed grooves so as to prevent removal of the pins.

8. An apparatus according to claim 6, wherein the pins are held firmly in place by means of an adhesive cover sheet.

9. An apparatus according to claim 6, wherein the pins are held firmly in place by means of an adhesive cover sheet and a respective removable tab for each pin projects radially outwardly of the cover sheet and each tab sheaths the tip of its respective pin.

10. An apparatus according to claim 6, wherein the pins are held firmly in place by means of an adhesive cover sheet and the cover sheet is formed in parts to render it more easy to place on the disc.

11. An apparatus according to claim 1, wherein each pin is individually numbered and the numbers of the pins are sequentially visible to an operator as each pin is located at its point of use.

12. An apparatus according to claim 1, wherein break means is provided so that once all pins have been used further movement of the pins is prevented.

* * * * *